United States Patent [19]

Cantatore et al.

[11] Patent Number: 4,608,436
[45] Date of Patent: Aug. 26, 1986

[54] PIPERIDINE COMPOUNDS

[75] Inventors: Giuseppe Cantatore, Bitonto; Valerio Borzatta, Bologna, both of Italy

[73] Assignee: Ciba-Geigy S.p.A., Origgio, Italy

[21] Appl. No.: 721,936

[22] Filed: Apr. 9, 1985

[30] Foreign Application Priority Data

Apr. 9, 1984 [IT] Italy .................. 20449 A/84

[51] Int. Cl.⁴ .................. C07D 401/12; C07D 401/14
[52] U.S. Cl. ....................... 546/188; 546/19; 546/187; 524/100
[58] Field of Search ............ 546/19, 187, 188

[56] References Cited

U.S. PATENT DOCUMENTS 3,920,659 11/1975 Ramey et al. ............ 260/268 TR
3,940,363 2/1976 Murayama et al. ........ 260/45.8 N
3,975,357 8/1976 Murayama et al. ........ 260/45.8 N
3,992,390 11/1976 Holt et al. .............. 260/293.82
4,110,305 8/1978 Holt et al. .............. 260/45.8 N Primary Examiner—Robert T. Bond
Attorney, Agent, or Firm—Wenderoth, Lind & Ponack

[57] ABSTRACT

Novel piperidine compounds having a stabilizing activity for organic material, especially for synthetic polymers, are of the formula

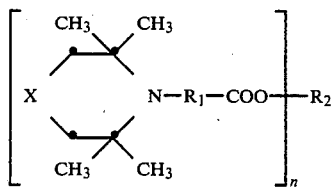

in which $R_1$, $R_2$, X and n are as defined in the text.

5 Claims, No Drawings

PIPERIDINE COMPOUNDS

The present invention relates to novel piperidine compounds and to their use as light stabilisers, heat stabilisers and oxidation stabilisers for organic material, especially for synthetic polymers.

In order to delay the negative effect of ultraviolet radiation on polymers, it has been proposed to use various stabilisers, which protect against light: in particular, the German "Auslegeschrift" No. 1 929 928 describes piperidyl esters of aliphatic and aromatic carboxylic acids.

The novel compounds are of the following general formula (I)

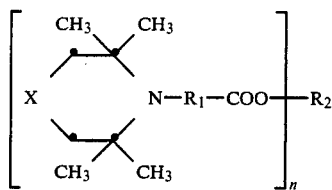

in which $R_1$ is $C_1$–$C_{12}$-alkylene, X is methylene, a group

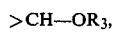

in which $R_3$ is hydrogen, $C_1$–$C_{18}$-alkyl, $C_3$–$C_{12}$-alkenyl, $C_7$–$C_{18}$-aralkyl or $C_1$–$C_{12}$-acyl, or X is

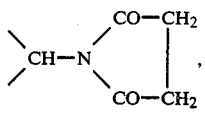

a group

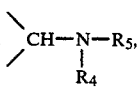

in which $R_4$ is hydrogen, $C_1$–$C_{18}$-alkyl, $C_1$–$C_{18}$-alkyl substituted by $C_1$–$C_{18}$-alkoxy or $C_2$–$C_{18}$-dialkylamino, or $R_4$ is $C_5$–$C_{18}$-cycloalkyl, $C_3$–$C_{18}$-alkenyl or $C_7$–$C_{18}$-aralkyl and $R_5$ is $C_1$–$C_{12}$-acyl or a group

—$COOR_6$ in which $R_6$ is $C_1$–$C_{12}$-alkyl or $C_3$–$C_{12}$-alkenyl, or X is a group

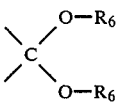

in which $R_6$ is as defined above or X is a group of the formula (II)

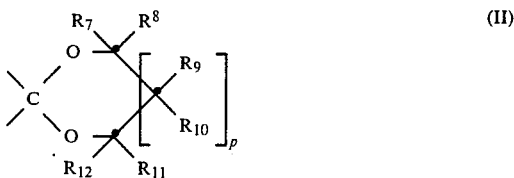

in which the radicals $R_7$–$R_{12}$ can be identical or different and are hydrogen or $C_1$–$C_4$-alkyl and p is zero or 1, n is 1 or 2 and, if n=1, $R_2$ is a group of the formula (III) or (IV)

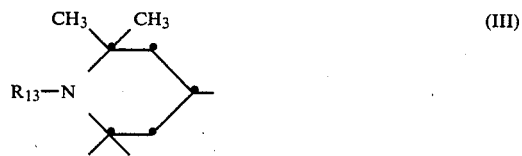

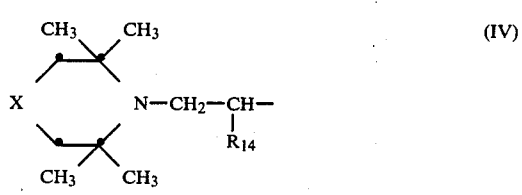

in which $R_{13}$ is hydrogen, O·, cyanomethyl, $C_1$–$C_{12}$-alkyl, $C_3$–$C_{12}$-alkenyl or -alkynyl, $C_7$–$C_{12}$-aralkyl or $C_1$–$C_{12}$-acyl, X is as defined above and $R_{14}$ is hydrogen, $C_1$–$C_6$-alkyl or $C_6$–$C_{12}$-aryl, or, if n=2, $R_2$ is a group of the formula (V)

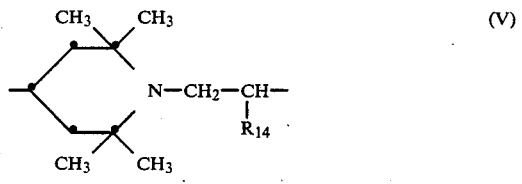

in which $R_{14}$ is as defined above.

Non-restrictive, illustrative examples of the meanings of the above radicals are as follows:

for $R_1$: methylene, ethylene, propylene, butylene, pentylene, hexylene, octylene, decylene and dodecylene;

for $R_3$: hydrogen, methyl, ethyl, propyl, butyl, pentyl, hexyl, octyl, 2-ethylhexyl, decyl, dodecyl, tetradecyl, hexadecyl, octadecyl, allyl, methallyl, 2-butenyl, 2-hexenyl, 10-undecenyl, benzyl, methylbenzyl, t-butylbenzyl, hydroxybenzyl, 4-hydroxy-3,5-di-t-butylbenzyl, acetyl, propionyl, butyryl, caproyl, lauroyl and benzoyl;

for $R_4$: hydrogen, methyl, ethyl, propyl, butyl, hexyl, octyl, decyl, dodecyl, tetradecyl, hexadecyl, octadecyl, 2-methoxyethyl, 2-ethoxyethyl, 3-methoxypropyl, 3-ethoxypropyl, 3-butoxypropyl, 3-octyloxypropyl, cyclohexyl, and methylcyclohexyl, trimethylcyclohexyl, cyclooctyl, cyclododecyl, allyl, methallyl, 2-butenyl, 2-hexenyl, 10-undecenyl, oleyl, benzyl, methylbenzyl, t-butylbenzyl, hydroxybenzyl and 4-hydroxy-3,5-di-t-butylbenzyl;

for $R_5$: acetyl, propionyl, butyryl, caproyl, lauroyl and benzoyl;

for $R_6$: methyl, ethyl, propyl, butyl, hexyl, octyl, decyl and dodecyl, allyl, 2-butenyl, 3-hexenyl;

for $R_7$–$R_{12}$: hydrogen, methyl, ethyl, propyl and butyl;

for $R_{13}$: hydrogen, cyanomethyl, O·, methyl, ethyl, propyl, butyl, hexyl, octyl, decyl, dodecyl, allyl, methallyl, 2-butenyl, 2-hexenyl, 10-undecenyl, propargyl, benzyl, methylbenzyl, t-butylbenzyl, hydroxybenzyl, acetyl, propionyl, butyryl, caproyl, lauroyl, benzoyl, acryloyl, methacryloyl and crotonyl; and for $R_{14}$: hydrogen, methyl, ethyl, propyl, butyl, phenyl, methylphenyl, dimethylphenyl and t-butylphenyl.

Those compounds of the formula (I) are preferred, in which $R_1$ is $C_1$–$C_6$-alkylene, X is methylene, a group

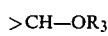

in which $R_3$ is hydrogen, $C_1$–$C_{12}$-alkyl, $C_3$–$C_6$-alkenyl, $C_7$–$C_9$-aralkyl or $C_1$–$C_6$-acyl, or a group

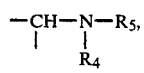

in which $R_4$ is hydrogen, $C_1$–$C_{12}$-alkyl, $C_1$–$C_{12}$-alkyl substituted by $C_1$–$C_{12}$-alkoxy or $C_2$–$C_{12}$-dialkylamino, or $R_4$ is $C_6$–$C_9$-cycloalkyl, $C_3$–$C_6$-alkenyl or $C_7$–$C_9$-aralkyl and $R_5$ is $C_1$–$C_6$-acyl or a group

—COOR$_6$ in which $R_6$ is $C_1$–$C_4$-alkyl or X is a group of the formula (II) in which $R_7$–$R_{12}$ are hydrogen, methyl or ethyl, n is 1 or 2 and, if n=1, $R_2$ is a group of the formula (III) or (IV), in which $R_{13}$ is hydrogen, $C_1$–$C_6$-alkyl, $C_3$–$C_6$-alkenyl or -alkynyl, benzyl or $C_1$–$C_6$-acyl, X is as defined above and $R_{14}$ is hydrogen, $C_1$–$C_4$-alkyl or phenyl, and if n=2, $R_2$ is a group of the formula (V) in which $R_{14}$ is as defined above.

Those compounds of the formula (I) are particularly preferred in which $R_1$ is methylene, X is methylene, a group

in which $R_3$ is $C_1$–$C_8$-alkyl or allyl, a group

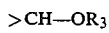

in which $R_4$ is $C_1$–$C_4$-alkyl and $R_5$ is $C_2$–$C_4$-acyl or X is a group

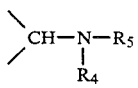

n is 1 or 2 and, if n=1, $R_2$ is a group of the formula (III) or (IV) in which $R_{13}$ is hydrogen or methyl, X is as defined above and $R_{14}$ is hydrogen or methyl, and, if n=2, $R_2$ is a group of the formula (V) in which $R_{14}$ is as defined above.

Compounds of the formula (I) which are of interest are those in which $R_1$ is methylene or propylene, X is methylene,

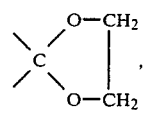

a group

>CHOR$_3$ in which $R_3$ is n-propyl, n-butyl, n-ocytl allyl, or X is a group

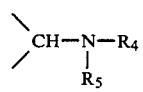

in which $R_4$ is ethyl or n-butyl and $R_5$ is acetyl or

—COOC$_2$H$_5$, n is 1 or 2 and, if n=1, $R_2$ is a group of the formula (III) or (IV) in which $R_{13}$ is hydrogen or methyl, X is

>CH—OC$_4$H$_9$ and $R_{14}$ is hydrogen, and if n=2, $R_2$ is a group of the formula (V) in which $R_{14}$ is hydrogen or methyl.

The compounds of the formula (I) can be prepared by reacting a compound of the formula (VI)

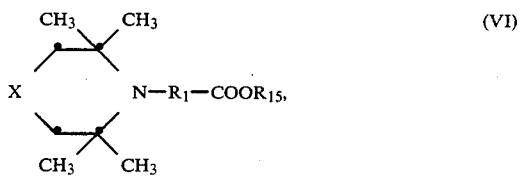

in which X and $R_1$ are as defined above and $R_{15}$ is $C_1$–$C_8$-alkyl, preferably $C_1$–$C_4$-alkyl, with, if n=1, a compound of the formula (VII) or (VIII)

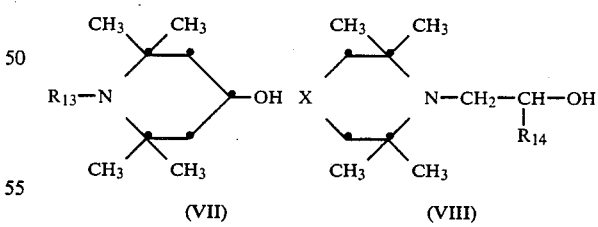

in which X, $R_{13}$ and $R_{14}$ are as defined above, or, if n=2, with a compound of the formula (IX)

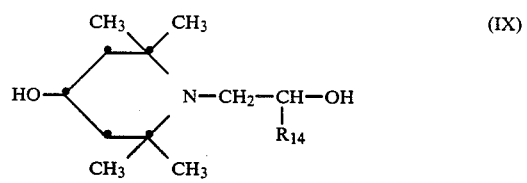

in which $R_{14}$ is as defined above.

The reaction can take place at a temperature from 100° to 250° C., preferably from 150° to 220° C., in the presence or absence of a solvent and in the presence of a suitable transesterification catalyst.

If the process is carried out with the use of a solvent, this can be selected from inert solvents, for example toluene, xylene, trimethylbenzene, ethylbenzene, tetralin, decalin or an aliphatic hydrocarbon having a boiling point between 100° and 220° C., the alcohol liberated during the reaction being distilled off.

The transesterification catalysts used can be alkali metals or their hydrides, amides, alkyl derivatives or alcoholates and furthermore, metal-organic compounds, such as titanium tetraisopropoxide, titanium tetrabutoxide and aluminium triisopropoxide.

If $n=1$, the molar ratio of the compound of formula (VI): compound of formula (VII) or (VIII) can be stoichiometric, i.e. 1:1, but it is preferable to use an excess of one of the two reagents, for example up to 20% of theory.

If $n=2$, the molar ratio of the compound of formula (VI): compound of formula (IX) can be stoichiometric, i.e. 2:1, but it is preferable to use an excess of the compounds of the formula (VI) for example up to 20% of theory.

The compounds of the formula (VI) can be obtained in accordance with known processes, by reacting a compound of the formula (X).

(X)

in which X is as defined above, with a halogenoester of the formula (XI)

$$Y-R_1-COOR_{15} \quad (XI)$$

in which Y is halogen, preferably chlorine or bromine, and $R_{15}$ is as defined above.

The compounds of the formulae (VII), (VIII) and (IX) are known compounds.

For illustrative purposes, the preparation of 1-(ethoxycarbonylmethyl)-2,2,6,6-tetramethylpiperidine is described.

Preparation of 1-(ethoxycarbonylmethyl)-2,2,6,6-tetramethylpiperidine 20 g of potassium iodide and 290 g (2.37 mol) of ethyl chloroacetate are added to 334 g (2.37 mol) of 2,2,6,6-tetramethylpiperidine dissolved in 650 ml of methyl ethyl ketone.

The mixture thus obtained is heated under reflux for 16 hours and then cooled, and 327 g (2.37 mol) of finely ground anhydrous potassium carbonate are added.

The mixture is again heated unter reflux for a further 16 hours and then cooled, filtered and evaporated in vacuo. The residue obtained is taken up in 600 ml of methylene chloride and the solution is washed with water. The organic solution is then dried over sodium sulfate and, after evaporation, the residue is distilled.

430.7 g of a product of boiling point=124°–126° C./17 mmHg are obtained.

The procedure is repeated analogously for preparing the following compounds of the formula (VI) which are used for the synthesis of compounds of the formula (I):

TABLE 1

| Compound of the formula (VI) | Boiling point (°C./mm Hg) |
|---|---|
| (H₂C—O / H₂C—O)CH— piperidine with N—CH₂COOC₂H₅ (2,2,6,6-tetramethyl) | 153–155/7 |
| C₄H₉—O— piperidine with N—CH₂COOC₂H₅ (2,2,6,6-tetramethyl) | 171–173/20 |
| H₂C=CH—CH₂—O— piperidine with N—CH₂COOC₂H₅ (2,2,6,6-tetramethyl) | 162–164/15 |

TABLE 1-continued

| Compound of the formula (VI) | Boiling point (°C./mm Hg) |
|---|---|
| n-C$_8$H$_{17}$—O—[2,2,6,6-tetramethylpiperidinyl]—N—CH$_2$COOC$_2$H$_5$ | 184–186/2 |
| C$_2$H$_5$—N(COCH$_3$)—[2,2,6,6-tetramethylpiperidinyl]—N—CH$_2$COOC$_2$H$_5$ | 172–174/1 |
| n-C$_4$H$_9$—N(COCH$_3$)—[2,2,6,6-tetramethylpiperidinyl]—N—CH$_2$COOC$_2$H$_5$ | 220–221/1.5 |

In order to illustrate the present invention more clearly, several examples of the preparation of compounds of the formula (I) are described below; these examples are given by way of illustration only and do not imply any restriction.

EXAMPLE 1

Preparation of

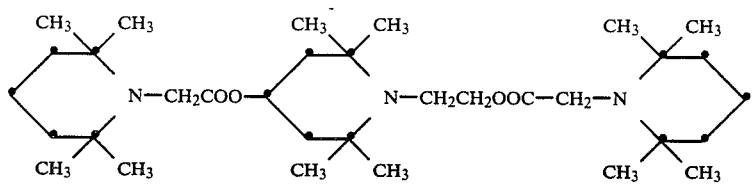

300 g (1.32 mol) of 1-(ethoxycarbonylmethyl)-2,2,6,6-tetramethylpiperidine and 5.7 g of titanium tetraisopropoxide are added to 120.6 g (0.6 mol) of 1-(2-hydroxyethyl)-4-hydroxy-2,2,6,6-tetramethylpiperidine.

The mixture is heated under a nitrogen stream for 3 hours at a temperature of 160°–170° C., for 4 hours at 190°–200° C., the ethanol liberated during the reaction (70.8 ml) being removed, and finally, for 1 hour at 160°–170° C. in vacuo (20 mmHg).

The reaction mixture is cooled, and 180 ml of petroleum ether (boiling point 60°–80° C.) are added; the precipitate obtained is separated off by filtration and recrystallised from petroleum ether (boiling point 60°–80° C.).

This gives the compound of the formula

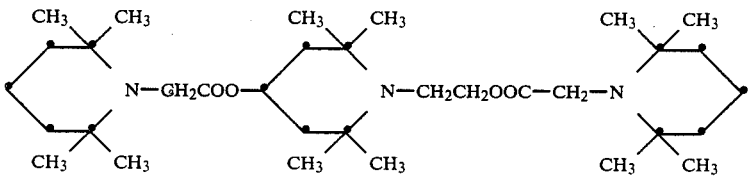

The product obtained melts at 143°–144° C.

Analysis for C$_{33}$H$_{61}$N$_3$O$_4$: Calculated: C 70.30% H 10.90% N 7.45%. Found: C 70.27% H 10.83% N 7.40%.

EXAMPLES 2–21

The procedure described in Example 1 is repeated for preparing the following compounds of the formula (I), using the appropriate intermediates of formula (VII), (VIII) or (IX).

TABLE 2

| Example No. | X | R₁ | R₂ | n | Melting point (°C.) Boiling point (°C./mm Hg) |
|---|---|---|---|---|---|
| 2 | H₂C—O, H₂C—O (spiro) | —CH₂— | 2,2,6,6-tetramethylpiperidin-4-yl (NH) | 1 | 135–136 |
| 3 | H₂C—O, H₂C—O (spiro) | —CH₂— | 1,2,2,6,6-pentamethylpiperidin-4-yl (N—CH₃) | 1 | 113–114 |
| 4 | n-C₄H₉O—CH< | —CH₂— | 2,2,6,6-tetramethylpiperidin-4-yl (NH) | 1 | 200–202/1.5 |
| 5 | n-C₄H₉O—CH< | —CH₂— | 1,2,2,6,6-pentamethylpiperidin-4-yl (N—CH₃) | 1 | 202–203/0.5 |
| 6 | H₂C=CH—CH₂—O—CH< | —CH₂— | 1,2,2,6,6-pentamethylpiperidin-4-yl (N—CH₃) | 1 | 193–194/0.4 |
| 7 | n-C₈H₁₇—O—CH< | —CH₂— | 2,2,6,6-tetramethylpiperidin-4-yl (NH) | 1 | 219–220/0.5 |
| 8 | n-C₈H₁₇—O—CH< | —CH₂— | 1,2,2,6,6-pentamethylpiperidin-4-yl (N—CH₃) | 1 | 225–226/0.4 |
| 9 | H₅C₂—N(COCH₃)—CH< | —CH₂— | 2,2,6,6-tetramethylpiperidin-4-yl (NH) | 1 | 132–133 |

TABLE 2-continued

| Example No. | X | R₁ | R₂ | n | Melting point (°C.) Boiling point (°C./mm Hg) |
|---|---|---|---|---|---|
| 10 | H₅C₂–N–CH< , COCH₃ | –CH₂– | (2,2,6,6-tetramethyl-1-methyl-piperidin-4-yl) ring with N–CH₃ | 1 | 113–114 |
| 11 | n-C₄H₉–N–CH< , COCH₃ | –CH₂– | (2,2,6,6-tetramethylpiperidin-4-yl) ring with NH | 1 | 153–154 |
| 12 | n-C₄H₉–N–CH< , COCH₃ | –CH₂– | (2,2,6,6-tetramethyl-1-methyl-piperidin-4-yl) ring with N–CH₃ | 1 | 244–246/0.8 |
| 13 | H₅C₂–N–CH< , COOC₂H₅ | –CH₂– | (2,2,6,6-tetramethylpiperidin-4-yl) ring with NH | 1 | resin |
| 14 | n-C₄H₉–O–CH< | –CH₂– | n-C₄H₉O–(2,2,6,6-tetramethylpiperidine) N–(CH₂)₂– | 1 | 233–235/0.4 |
| 15 | n-C₃H₇O–CH< | –(CH₂)₃– | (2,2,6,6-tetramethylpiperidin-4-yl) ring with NH | 1 | 215–216/0.2 |
| 16 | H₂C–O\ >< /  H₂C–O | –CH₂– | (2,2,6,6-tetramethylpiperidin-4-yl) ring with N–(CH₂)₂– | 2 | 173–174 |
| 17 | n-C₄H₉–O–CH< | –CH₂– | (2,2,6,6-tetramethylpiperidin-4-yl) ring with N–(CH₂)₂– | 2 | 118–119 |

TABLE 2-continued

| Example No. | X | R$_1$ | R$_2$ | n | Melting point (°C.) Boiling point (°C./mm Hg) |
|---|---|---|---|---|---|
| 18 | H$_2$C=CH—CH$_2$—O—CH< | —CH$_2$— | 2,2,6,6-tetramethylpiperidin-1-yl—(CH$_2$)$_2$— | 2 | 102–103 |
| 19 | H$_5$C$_2$—N(COCH$_3$)—CH< | —CH$_2$— | 2,2,6,6-tetramethylpiperidin-1-yl—(CH$_2$)$_2$— | 2 | 186–187 |
| 20 | n-C$_4$H$_9$—N(COCH$_3$)—CH< | —CH$_2$— | 2,2,6,6-tetramethylpiperidin-1-yl—(CH$_2$)$_2$— | 2 | 138–139 |
| 21 | H$_5$C$_2$—N(COCH$_3$)—CH< | —CH$_2$— | 2,2,6,6-tetramethylpiperidin-1-yl—CH$_2$—CH(CH$_3$)— | 2 | 137–138 |

As mentioned at the outset, the compounds of the formula (I) are very effective in improving the light stability, heat stability and oxidation stability of synthetic polymers, for example high-density and low-density polyethylene, polypropylene, ethylene/propylene copolymers, ethylene/vinyl acetate copolymers, polybutadiene, polyisoprene, polystyrene, butadiene/styrene copolymers, vinyl chloride/vinylidene chloride polymers and copolymers, polyoxymethylene, polyurethane, saturated and unsaturated polyesters, polyamides, polycarbonates, polyacrylates, alkyd resins and epoxide resins.

The compounds of the formula (I) can be mixed with organic material, e.g. with synthetic polymers in various proportions depending on the nature of the polymer, the end use and the presence of other additives. In general, it is advantageous to employ from 0.01 to 5% weight of the compounds of the formula (I), relative to the weight of the polymers, preferably from 0.05 to 1%. The compounds of the formula (I) can be incorporated into the polymeric materials by various processes, such as dry blending in the form of powders, or wet mixing in the form of solutions or suspensions, or mixing in the form of masterbatch; in these operations, the polymer can be employed in the form of powder, granules, a solution, a suspension or in the form of a latex.

The organic material stabilised with the products of the formula (I) can be used for the preparation of moulded articles, films, tapes, fibres, monofilaments, surface-coatings and the like.

If desired, other additives, such as antioxidants, ultraviolet absorbers, nickel stabilisers, pigments, fillers, plasticisers, antistatic agents, flameproofing agents, lubricants, anti-corrosion agents and metal deactivators, can be added to the mixtures of the compounds of the formula (I) with the polymers.

Examples of additives which can be mixed with the compounds of the formula (I) are, in particular:

Phenolic antioxidants, for example 2,6-di-t-butyl-p-cresol, 4,4'-thio-bis-(3-methyl-6-t-butylphenol)-1,1,3-tris(2-methyl-4-hydroxy-5-t-butylphenyl)-butane, octadecyl-3-(3,5-di-t-butyl-4-hydroxyphenyl)-propionate, pentaerythritol tetrakis-3-(3,5-di-t-butyl-4-hydroxyphenyl)-propionate, tris-(3,5-di-t-butyl-4-hydroxybenzyl)isocyanurate, tris-(4-t-butyl-3-hydroxy-2,6-dimethylbenzyl)isocyanurate and calcium monoethyl 3,5-di-t-butyl-4-hydroxybenzylphosphonate;

Secondary antioxidants, such as esters of thiodipropionic acid, for example di-n-dodecyl thiodipropionate and di-n-octadecyl thiodipropionate; aliphatic sulfides and disulfides, for example di-n-dodecyl sulfide, di-n-octadecyl sulfide and di-n-octadecyl disulfide; aliphatic, aromatic or aliphatic-aromatic phosphites and thiophosphites, for example tri-n-dodecyl phosphite, tris-(nonylphenyl)phosphite, tri-n-dodecyl trithiophosphite, phenyl di-n-decyl phosphite, di-n-octadecyl pentaerythritol diphosphite, tris-(2,4-di-t-butylphenyl)phosphite and tetrakis-(2,4-di-t-butylphenyl) 4,4'-biphenylenephosphonite;

Ultraviolet absorbers, for example 2-hydroxy-4-n-octyloxybenzophenone, 2-hydroxy-4-n-dodecyloxybenzophenone, 2-(2-hydroxy-3,5-di-t-butylphenyl)-5-chlorobenzotriazole, 2-(2-hydroxy-3,5-di-t-amylphenyl)-benzotriazole, 2,4-di-t-butylphenyl-3,5-di-t-butyl-4-hydroxybenzoate, hexadecyl 3,5-di-t-butyl-4-hydroxybenzoate, phenyl salicylate, p-t-butylphenyl salicylate, 2-ethoxy-2'-ethyl-oxanilide, 2-ethoxy-5-t-butyl-2'-ethyl-oxanilide, 2-ethoxy-2'-ethyl-5,5'-di-t- butyl-oxanilide and N'-(p-ethoxycarbonylphenyl)-N-ethyl-N-phenylformamidine;

Hindered amine-type light stabilisers, for example 2,2,6,6-tetramethyl-piperidin-4-yl benzoate, bis-(2,2,6,6-tetramethyl-piperidin-4-yl)sebacate, bis-(1,2,2,6,6-pentamethyl-piperidin-4-yl)sebacate, bis-(1,2,2,6,6-pentamethyl-piperidin-4-yl)butyl-3,5-di-t-butyl-4-hydroxybenzylmalonate, piperidinyl derivatives of triazine polymers of the type described in U.S. Pat. No. 4,086,204 and piperidine polyesters of the type described in U.S. Pat. No. 4,233,412, 2,2,4,4-tetramethyl-7-oxa-3,20-diazaspiro[5.1.11.2]heneicosan-21-one and 1,1'ethylene-bis-(3,3,5,5-tetramethylpiperazinone);

Light stabilisers based on nickel, for example Ni monoethyl 3,5-di-t-butyl-4-hydroxybenzyl-phosphonate, the butylamine-Ni 2,2'-thio-bis-(4-t-octylphenolate) complex, Ni 2,2'-thio-bis-(4-t-octylphenolate), Ni dibutyldithiocarbamate, Ni 3,5-di-t-butyl-4-hydroxybenzoate and the Ni complex of 2-hydroxy-4-n-octyloxybenzophenone;

Organo-tin-stabilisers, for example dibutyl-tin maleate, dibutyl-tin laurate and dioctyl-tin maleate;

Acrylic esters, for example ethyl α-cyano-β,β-diphenylacrylate and methyl α-cyano-β-methyl-4-methoxycinnamate;

Metal salts of higher fatty acids, for example calcium stearate, barium stearate, cadmium stearate, zinc stearate, lead stearate, nickel-stearate, magnesium behenate, calcium behenate, barium behenate, zinc behenate, calcium laurate, cadmium laurate, zinc laurate and barium laurate;

Organic and inorganic pigments, for example Colour Index Pigment Yellow 37, Colour Index Pigment Yellow 83, Colour Index Pigment Red 144, Colour Index Pigment Red 48:3, Colour Index Pigment Blue 15, Colour Index Pigment Green 7, titanium dioxide, iron oxide and the like.

The efficiency, as stabilisers, of the products prepared according to the invention is illustrated in the examples which follow, in which some products obtained in the preparation examples are used for stabilising polypropylene tapes and plates.

EXAMPLE 22

2 g of each of the compounds indicated in Table 3, 1 g of pentaerythritol tetrakis-3-(3,5-di-t-butyl-4-hydroxyphenyl)propionate (antioxidant) and 1 g of calcium stearate are intimately mixed with 1,000 g of polypropylene powder of melt index 3 (Propathene HF 18, a product of Imperial Chemical Industries, registered trademark).

The mixture obtained is then extruded at a temperature of 200°–230° C. and converted into granules from which tapes of 40 μm thickness and 3 mm with are obtained, under the following working conditions:
 extruder temperature: 230°–240° C.
 head temperature: 240° C.
 stretch ratio: 1:6

The tapes thus prepared are exposed, mounted on a white card, in a 65 WR model Weather-Ometer (ASTM G 27-70), with a black panel temperature of 63° C.

The residual tenacity is measured on samples, taken after various times of exposure to light, by means of a constant-speed tensometer; the exposure time in hours ($T_{50}$) needed to halve the initial tenacity is then calculated.

For comparison, polypropylene tapes prepared under the same conditions as indicated above, but without the addition of the compounds of the invention, are exposed.

The results obtained are shown in Table 3:

TABLE 3

| Stabiliser | $T_{50}$ (hours) |
|---|---|
| none | 220 |
| Compound of Example 1 | 1,960 |
| Compound of Example 2 | 2,640 |
| Compound of Example 4 | 2,990 |
| Compound of Example 5 | 2,250 |
| Compound of Example 6 | 2,830 |
| Compound of Example 7 | 1,860 |
| Compound of Example 8 | 2,550 |
| Compound of Example 9 | 2,340 |
| Compound of Example 10 | 2,320 |
| Compound of Example 11 | 2,000 |
| Compound of Example 12 | 2,290 |
| Compound of Example 18 | 2,000 |
| Compound of Example 19 | 1,890 |
| Compound of Example 21 | 1,790 |

EXAMPLE 23

1.0 g of each of the products indicated in Table 4, 1 g of pentaerythritol tetrakis-3-(3,5-di-t-butyl-4-hydroxyphenyl)propionate, 1 g of calcium stearate, 1 g of Blue Phtalocyanine and 1.000 g of polypropylene powder of melt index 3 (Propathene HF 18, a product of Imperial Chemical Industries) are intimately mixed in a slow mixer.

The mixtures obtained are extruded at a temperature of 200°–220° C. to give granules of polymer, which are then converted into 2 mm thick sheets by die extrusion at 250° C.

The sheets obtained are exposed in a 65 WR model Weather-Ometer (ASTM G 27-70), with a black panel temperature of 63° C., up to the onset of surface embrittlement (chalking).

For comparison, a polypropylene sheet prepared under the same conditions as indicated above, but without the addition of the compounds according to the invention, is exposed.

The exposure time (in hours) required for such an onset or embrittlement is indicated in Table 4.

TABLE 4

| Stabiliser | Embrittlement time (hours) |
|---|---|
| none | 500 |
| Compound of Example 1 | 2,410 |
| Compound of Example 3 | 2,910 |
| Compound of Example 4 | 3,260 |
| Compound of Example 5 | 3,260 |
| Compound of Example 7 | 3,260 |
| Compound of Example 8 | 3,440 |
| Compound of Example 9 | 3,260 |
| Compound of Example 10 | 3,100 |
| Compound of Example 11 | 3,100 |
| Compound of Example 12 | 3,100 |
| Compound of Example 16 | 2,710 |
| Compound of Example 17 | 2,410 |

What we claim is:

1. A compound of the formula (I)

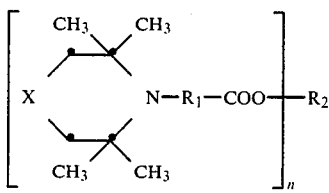

in which $R_1$ is $C_1$–$C_{12}$-alkylene, X is methylene, a group $$>CH—OR_3,$$

in which $R_3$ is hydrogen, $C_1$–$C_{18}$-alkyl, $C_3$–$C_{12}$-alkenyl, $C_7$–$C_{18}$-aralkyl or $C_1$–$C_{12}$-acyl, or X is a group

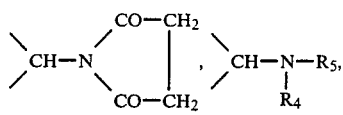

in which $R_4$ is hydrogen, $C_1$–$C_{18}$-alkyl, $C_1$–$C_{18}$-alkyl substituted by $C_1$–$C_{18}$-alkoxy or $C_2$–$C_{18}$-dialkylamino, or $R_4$ is $C_5$–$C_{18}$-cycloalkyl, $C_3$–$C_{18}$-alkenyl or $C_7$–$C_{18}$-aralkyl and $R_5$ is $C_1$–$C_{12}$-acyl or a group $$—COOR_6$$

in which $R_6$ is $C_1$–$C_{12}$-alkyl or $C_3$–$C_{12}$-alkenyl, or X is a group

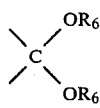

in which $R_6$ is as defined above or X is a group of the formula (II)

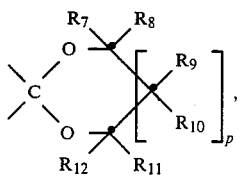

in which the radicals $R_7$–$R_{12}$ can be identical or different and are hydrogen or $C_1$–$C_4$-alkyl and p is zero or 1, n is 1 or 2 and, if n=1, $R_2$ is a group of the formula (III) or (IV)

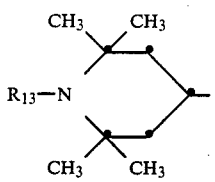

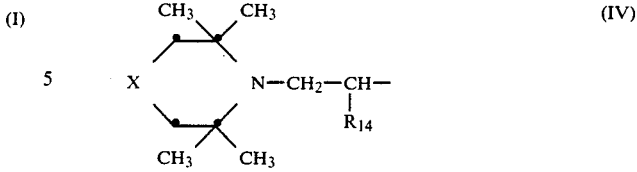

in which $R_{13}$ is hydrogen, O·, cyanomethyl, $C_1$–$C_{12}$-alkyl, $C_3$–$C_{12}$-alkenyl or -alkynyl, $C_7$–$C_{12}$-aralkyl or $C_1$–$C_{12}$-acyl, X is as defined above and $R_{14}$ is hydrogen, $C_1$–$C_6$-alkyl or $C_6$–$C_{12}$-aryl, or, if n=2, $R_2$ is a group of the formula (V)

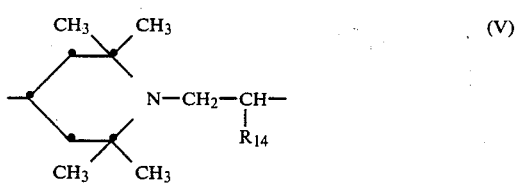

in which $R_{14}$ is as defined above.

2. A compound of the formula (I) according to claim 1, in which $R_1$ is $C_1$–$C_6$-alkylene, X is methylene, a group $$>CH—OR_3$$

in which $R_3$ is hydrogen, $C_1$–$C_{12}$-alkyl, $C_3$–$C_6$-alkenyl, $C_7$–$C_9$-aralkyl or $C_1$–$C_6$-acyl, or a group

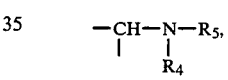

in which $R_4$ is hydrogen, $C_1$–$C_{12}$-alkyl, $C_1$–$C_{12}$-alkyl substituted by $C_1$–$C_{12}$-alkoxy or $C_2$–$C_{12}$-dialkylamino, or $R_4$ is $C_6$–$C_9$-cycloalkyl, $C_3$–$C_6$-alkenyl or $C_7$–$C_9$-aralkyl and $R_5$ is $C_1$–$C_6$-acyl or a group $$—COOR_6$$

in which $R_6$ is $C_1$–$C_4$-alkyl or X is a group of the formula (II) in which $R_7$–$R_{12}$ are hydrogen, methyl or ethyl, n is 1 or 2 and, if n=1, $R_2$ is a group of the formula (III) or (IV) in which $R_{13}$ is hydrogen, $C_1$–$C_6$-alkyl, $C_3$–$C_6$-alkenyl or -alkynyl, benzyl or $C_1$–$C_6$-acyl, X is as defined above and $R_{14}$ is hydrogen, $C_1$–$C_4$-alkyl or phenyl, and if n=2, $R_2$ is a group of the formula (V) in which $R_{14}$ is as defined above.

3. A compound of the formula (I) according to claim 1, in which $R_1$ is methylene, X is methylene, a group $$>CH—OR_3$$

in which $R_3$ is $C_1$–$C_8$-alkyl or allyl, a group

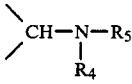

in which $R_4$ is $C_1$–$C_4$-alkyl and $R_5$ is $C_2$–$C_4$-acyl or X is a group

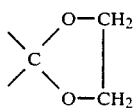

n is 1 or 2 and, if n=1, $R_2$ is a group of the formula (III) or (IV) in which $R_{13}$ is hydrogen or methyl, X is as defined above and $R_{14}$ is hydrogen or methyl, and, if n=2, $R_2$ is a group of the formula (V) in which $R_{14}$ is as defined above.

4. A compound of the formula (I) according to claim 1, in which $R_1$ is methylene or propylene, X is methylene,

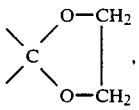

a group

>CHOR_3 in which $R_3$ is n-propyl, n-butyl, n-octyl or allyl, or X is a group

>CH—N—R_4
     |
     R_5 in which $R_4$ is ethyl or n-butyl and $R_5$ is acetyl or

—COOC_2H_5, n is 1 or 2 and, if n=1, $R_2$ is a group of the formula (III) or (IV) in which $R_{13}$ is hydrogen or methyl, X is

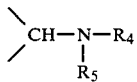

and $R_{14}$ is hydrogen, and if n=2, $R_2$ is a group of the formula (V) in which $R_{14}$ is hydrogen or methyl.

5. A compound according to claim 1 of the formulae

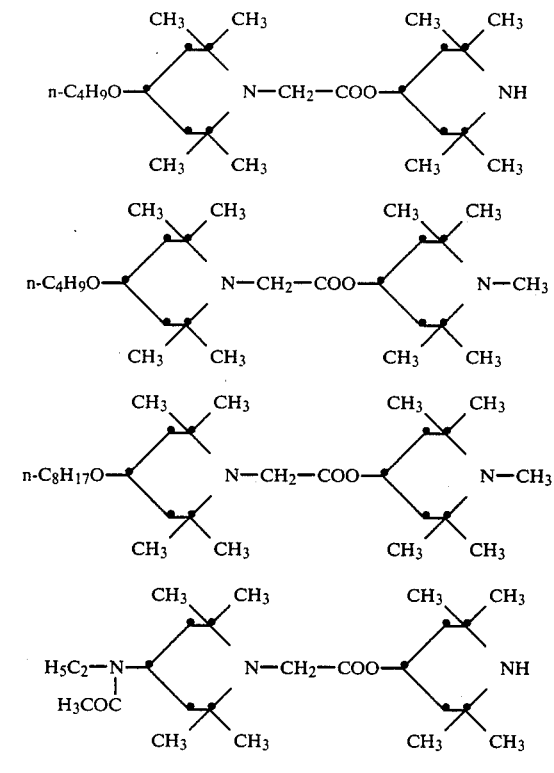

* * * * *